(12) United States Patent
Kresnyak

(10) Patent No.: US 9,315,452 B2
(45) Date of Patent: Apr. 19, 2016

(54) PROCESS FOR CO-PRODUCING COMMERCIALLY VALUABLE PRODUCTS FROM BYPRODUCTS OF FISCHER-TROPSCH PROCESS FOR HYDROCARBON FUEL FORMULATION IN A GTL ENVIRONMENT

(71) Applicant: Expander Energy Inc., Calgary (CA)

(72) Inventor: Steve Kresnyak, Calgary (CA)

(73) Assignee: Expander Energy Inc., Calgary (CA)

(*) Notice: Subject to any disclaimer, the term of this patent is extended or adjusted under 35 U.S.C. 154(b) by 0 days.

(21) Appl. No.: 14/540,084

(22) Filed: Nov. 13, 2014

(65) Prior Publication Data

US 2015/0141535 A1    May 21, 2015

Related U.S. Application Data

(63) Continuation-in-part of application No. 13/228,042, filed on Sep. 8, 2011, now Pat. No. 8,889,746.

(51) Int. Cl.

| | | |
|---|---|---|
| C07C 27/00 | (2006.01) | |
| C07C 273/00 | (2006.01) | |
| C07C 273/04 | (2006.01) | |
| C01C 1/04 | (2006.01) | |
| C01B 3/38 | (2006.01) | |
| C10L 1/04 | (2006.01) | |
| C10G 2/00 | (2006.01) | |
| C10G 45/02 | (2006.01) | |
| C10G 45/58 | (2006.01) | |
| C10G 47/00 | (2006.01) | |
| C10G 47/22 | (2006.01) | |
| C10K 1/00 | (2006.01) | |
| C10K 1/08 | (2006.01) | |
| C10K 1/32 | (2006.01) | |
| C07C 29/151 | (2006.01) | |

(52) U.S. Cl.
CPC .............. *C07C 273/04* (2013.01); *C01B 3/38* (2013.01); *C01B 3/382* (2013.01); *C01C 1/04* (2013.01); *C07C 29/1518* (2013.01); *C10G 2/30* (2013.01); *C10G 45/02* (2013.01); *C10G 45/58* (2013.01); *C10G 47/00* (2013.01); *C10G 47/22* (2013.01); *C10K 1/005* (2013.01); *C10K 1/08* (2013.01); *C10K 1/32* (2013.01); *C10L 1/04* (2013.01); C01B 2203/0233 (2013.01); C01B 2203/0244 (2013.01); C01B 2203/0405 (2013.01); C01B 2203/0435 (2013.01); C01B 2203/0475 (2013.01); C01B 2203/062 (2013.01); C01B 2203/0844 (2013.01); C01B 2203/0872 (2013.01); C01B 2203/1241 (2013.01); C01B 2203/1258 (2013.01); C01B 2203/142 (2013.01); C01B 2203/143 (2013.01); C01B 2203/145 (2013.01); C01B 2203/147 (2013.01); C10G 2300/1022 (2013.01); C10L 2200/0492 (2013.01); C10L 2290/42 (2013.01)

(58) Field of Classification Search
CPC ............ C10G 2/30; C10G 2300/1022; C10G 2300/1077; C10G 2300/206; C10G 2300/42; C10K 3/006; C10K 3/005; C07C 273/04; C01B 2203/0233; C01B 2203/0244; C01B 2203/025; C01B 2203/0283
USPC ........ 518/700, 702, 705; 564/67, 69; 423/359
See application file for complete search history.

(56) References Cited

U.S. PATENT DOCUMENTS

| | | |
|---|---|---|
| 2,574,469 A | 11/1951 | Dressler et al. |
| 3,351,563 A | 11/1967 | Negra et al. |
| 3,941,820 A | 3/1976 | Jackson et al. |
| 4,217,112 A | 8/1980 | Johanson |
| 4,234,412 A | 11/1980 | Boersma et al. |
| 4,806,699 A | 2/1989 | Smith |
| 5,378,348 A | 1/1995 | Davis et al. |
| 5,494,653 A | 2/1996 | Paisley |
| 6,043,288 A | 3/2000 | DeGeorge et al. |
| 6,048,449 A | 4/2000 | Bogdan et al. |
| 6,183,627 B1 | 2/2001 | Friday et al. |
| 6,241,874 B1 | 6/2001 | Wallace et al. |
| 6,306,917 B1 | 10/2001 | Bohn et al. |
| 6,310,108 B1 | 10/2001 | Bonneau |
| 6,395,944 B1 | 5/2002 | Griffiths et al. |
| 6,512,018 B2 | 1/2003 | Kennedy |
| 6,531,516 B2 | 3/2003 | Davis et al. |
| 6,540,023 B2 | 4/2003 | Davis et al. |
| RE38,170 E | 7/2003 | DeGeorge et al. |
| 6,596,780 B2 | 7/2003 | Jahnke et al. |
| 6,602,404 B2 | 8/2003 | Walsh et al. |
| 6,656,343 B2 | 12/2003 | Dancuart |
| 6,693,138 B2 | 2/2004 | O'Rear |

(Continued)

FOREIGN PATENT DOCUMENTS

| | | |
|---|---|---|
| CA | 2320509 | 8/1999 |
| CA | 2595880 | 12/2005 |

(Continued)

OTHER PUBLICATIONS

S. Rossini, FT Gasifier Integration and Scale, Summer School "Next Generation Biofuels", Sep. 2009, p. 1-102, Bologna.

(Continued)

*Primary Examiner* — Jafar Parsa
(74) *Attorney, Agent, or Firm* — MBM Intellectual Property Law LLP

(57) ABSTRACT

The present invention is directed to the modification of the hydrocarbon production sequence of operations including the Fischer-Tropsch process for the production of hydrocarbon fuels in an efficient manner, along with the production of commercially valuable co-products from by-products of the hydrocarbon production process.

16 Claims, 11 Drawing Sheets

(56) References Cited

U.S. PATENT DOCUMENTS

| | | |
|---|---|---|
| 6,696,501 B2 | 2/2004 | Schanke et al. |
| 6,702,936 B2 | 3/2004 | Rettger et al. |
| 6,730,285 B2 | 5/2004 | Aasberg-Petersen et al. |
| 6,765,025 B2 | 7/2004 | Ding et al. |
| 6,863,802 B2 | 3/2005 | O'Rear et al. |
| 6,872,753 B2 | 3/2005 | Landis et al. |
| 6,958,363 B2 | 10/2005 | Espinoza et al. |
| 7,004,985 B2 | 2/2006 | Wallace et al. |
| 7,168,265 B2 | 1/2007 | Briscoe et al. |
| 7,208,530 B2 | 4/2007 | Norbeck et al. |
| 7,214,720 B2 | 5/2007 | Bayle et al. |
| 7,381,320 B2 | 6/2008 | Iqbal et al. |
| 7,407,571 B2 | 8/2008 | Rettger et al. |
| 7,413,647 B2 | 8/2008 | Calderon et al. |
| 7,566,394 B2 | 7/2009 | Koseoglu |
| 7,677,309 B2 | 3/2010 | Shaw et al. |
| 7,708,877 B2 | 5/2010 | Farshid et al. |
| 7,749,378 B2 | 7/2010 | Iqbal et al. |
| 7,776,114 B2 | 8/2010 | Rüger et al. |
| 7,795,317 B2 | 9/2010 | Eilers et al. |
| 7,795,318 B2 | 9/2010 | Van Hardeveld |
| 7,846,979 B2 | 12/2010 | Rojey et al. |
| 7,855,235 B2 | 12/2010 | Van Hardeveld |
| 7,863,341 B2 | 1/2011 | Routier |
| 7,879,919 B2 | 2/2011 | Ernst et al. |
| 2001/0051662 A1 | 12/2001 | Arcuri et al. |
| 2004/0091409 A1 | 5/2004 | Allison |
| 2004/0181313 A1 | 9/2004 | Mohedas et al. |
| 2005/0113464 A1 | 5/2005 | O'Rear et al. |
| 2005/0173305 A1* | 8/2005 | Smith ............................ 208/434 |
| 2005/0250862 A1 | 11/2005 | Bayle et al. |
| 2006/0167118 A1 | 7/2006 | Tijm et al. |
| 2006/0231455 A1 | 10/2006 | Olsvik et al. |
| 2008/0021119 A1 | 1/2008 | Norbeck et al. |
| 2008/0021122 A1 | 1/2008 | Norbeck et al. |
| 2008/0115415 A1 | 5/2008 | Agrawal et al. |
| 2008/0116111 A1 | 5/2008 | Newton |
| 2009/0084707 A1 | 4/2009 | Gil et al. |
| 2009/0186952 A1* | 7/2009 | Steynberg et al. ............ 518/704 |
| 2009/0200209 A1 | 8/2009 | Sury et al. |
| 2009/0261587 A1 | 10/2009 | Lomax et al. |
| 2009/0292571 A1 | 11/2009 | Gil et al. |
| 2010/0000153 A1 | 1/2010 | Kurkjian et al. |
| 2010/0036181 A1 | 2/2010 | Diebold et al. |
| 2010/0113624 A1 | 5/2010 | Routier et al. |
| 2010/0137458 A1 | 6/2010 | Erling et al. |
| 2010/0144905 A1 | 6/2010 | Reaveley et al. |
| 2010/0216898 A1 | 8/2010 | Tonseth et al. |
| 2011/0009501 A1 | 1/2011 | Ernst et al. |
| 2011/0049016 A1 | 3/2011 | McGrady et al. |
| 2012/0152120 A1 | 6/2012 | Davis et al. |
| 2012/0208902 A1 | 8/2012 | Kresnyak et al. |

FOREIGN PATENT DOCUMENTS

| | | |
|---|---|---|
| CA | 2657656 | 1/2008 |
| CA | 2731376 | 6/2010 |
| CN | 101223103 | 1/2011 |
| EP | 1608924 | 9/2007 |
| JP | 2002060762 | 2/2002 |
| JP | 2003183004 | 7/2003 |
| JP | 2007512328 | 5/2007 |
| JP | 2007297443 | 11/2007 |
| WO | WO2005000736 | 1/2005 |
| WO | WO2006081033 | 8/2006 |
| WO | WO2010119973 | 8/2006 |

OTHER PUBLICATIONS

Ronald (Ron) F. Colwell, P.E., Oil Refinery Processes, Process Engineering Associates, LLC, 2009, pp. 1-36.

Review of Technologies for Gasification of Biomass and Wastes, NNFCC Project 09/008, Jun. 2009, pp. 1-126.

Harold Boerrigter et al., Green Diesel from Biomass by Fischer-Tropsch Synthesis: New Insights Gas Cleaning and Process Design, Oct. 2002, pp. 1-15.

An Information Guide on Pursuing Biomass Energy Opportunities and Technologies in British Columbia, Biocap, Feb. 7, 2008, pp. 1-80, British Columbia.

Schaberg, Paul, Application of Synthetic Diesel Fuels, Sasol, Aug. 2005, pp. 1-16, Chicago.

SynDiesel B5 Synthetically made Diesel Fuel, with a 60 Cetane Rating, Storage Life of up to 10 years and 10% more BTU"s than Conventional Diesel, Feb. 14, 2011, pp. 1-2.

Service Offering from Axens IFP Group Technologies, Feb. 2, 2011, p. 1.

Office Action dated Nov. 6, 2014 for U.S. Appl. No. 13/887,342.

Office Action dated Jan. 26, 2015 for U.S. Appl. No. 13/887,342.

Office Action dated Nov. 6, 2014 for U.S. Appl. 13/024,925.

Stockle, M. et al., Dealing with Dieselization, Hydrocarbon Processing, Feb. 2010, vol. 89, Issue 2, pp. 55-60.

Office Action dated May 4, 2015 for U.S. Appl. No. 13/887,342.

Notice of Allowance dated Jul. 8, 2015 for U.S. Appl. No. 13/024,925.

* cited by examiner

PROCESS FOR CO-PRODUCING COMMERCIALLY VALUABLE PRODUCTS FROM BYPRODUCTS OF FISCHER-TROPSCH PROCESS FOR HYDROCARBON FUEL FORMULATION IN A GTL ENVIRONMENT

CROSS-REFERENCE TO RELATED APPLICATION

This application is a continuation-in-part of U.S. application Ser. No. 13/228,042, filed Sep. 8, 2011. The contents in the aforementioned application are hereby expressly incorporated by reference in its entirety and for all purposes.

TECHNICAL FIELD

The present invention relates to the modification of the Fischer-Tropsch sequence of operations including the Fischer-Tropsch process for the production of hydrocarbon fuels in an efficient manner, along with the production of commercially valuable co-products from by-products of the hydrocarbon production process.

BACKGROUND OF THE INVENTION

In the prior art, the Fischer-Tropsch process has been used for decades to assist in the formulation of hydrocarbons. In the last several years, this has become a concern given the escalating environmental concerns regarding poor fuel quality and pollution, together with the increasing costs of hydrocarbon exploration and refining. The major producers in this area have expanded the art significantly in this technological area with a number of patented advances and pending applications in the form of publications.

In the art, advances made in terms of the raw materials that have been progenitor materials for the Fischer-Tropsch process, have included, for example, coal-to-liquid (CTL), bio-to-liquid (BTL) and gas-to-liquid (GTL). One of the more particularly advantageous features of the gas-to-liquid (GTL) technology is the fact that it presents a possibility to formulate a higher value environmentally beneficial synthetic diesel product or syndiesel from stranded natural gas reserves, which would otherwise have not been commercially feasible to bring to market. As is generally known, the Fischer-Tropsch (FT) process converts hydrogen and carbon monoxide (commonly known as syngas) into liquid hydrocarbon fuels, examples of which include synthetic diesel, naphtha, kerosene, aviation or jet fuel and paraffinic wax. As a precursory step, the natural gas is thermally converted using heat and pressure in the presence of catalyst to produce a hydrogen rich syngas containing hydrogen and carbon monoxide. As a result of the Fischer-Tropsch technique, the synthetic fuels are very appealing from an environmental point of view, since they are paraffinic in nature and substantially devoid of contamination. This is particularly true in the case of the diesel fuel synthesis where the synthetic product has ideal properties for diesel engines, including extremely high cetane rating>70, negligible aromatics and sulphur content, in addition to enabling optimum combustion and virtually emission free operation. Synthetic diesel or syndiesel fuels significantly reduce nitrous oxide and particulate matter when compared with petroleum based diesel fuel.

U.S. Pat. No. 6,958,363 (Espinoza, et al.) teaches a process for synthesizing hydrocarbons where initially, a synthesis gas stream is formulated in a syngas generator. The synthesis gas stream comprises primarily hydrogen and carbon monoxide. The process involves catalytically converting the synthesis gas stream in a synthesis reaction to produce hydrocarbons and water followed by the generation of hydrogen-rich stream in the hydrogen generator. The process indicates that the hydrogen generator is separate from the syngas generator (supra) and that the hydrogen generator comprises either a process for converting hydrocarbons to olefins, a process for catalytically dehydrogenating hydrocarbons, or a process for refining petroleum, and a process for converting hydrocarbons to carbon filaments. The final step in the process in its broadest sense, involves consumption of hydrogen from the hydrogen-rich stream produced in one or more processes that result and increase value of the hydrocarbons or the productivity of the conversion of the hydrocarbons from the earlier second mentioned step.

Although a useful process, it is evident from the disclosure of Espinoza et al. that there is a clear intent to create olefins such as ethylene and propylene for petrochemical use, and aromatics for gasoline production. Additionally, there is a reforming step indicated to include the reformation of naphtha feedstock to generate a net surplus hydrogen by-product which is then recombined into the process. The naphtha is subsequently converted to aromatics for high octane gasoline blend stock.

U.S. Pat. No. 7,214,720 (Bayle et al.) discloses the production of liquid fuels by a concatenation of processes for treatment of a hydrocarbon feedstock. It is indicated in the disclosure that the liquid fuels begin with the organic material, typically biomass as a solid feedstock. The process involves a stage for the gasification of the solid feedstock, a stage for purification of synthesis gas and subsequently a stage for transformation of the synthesis gas into a liquid fuel.

This reference indicates in column 2 the essence of the technology:

"A process was found for the production of liquid fuels starting from a solid feedstock that contains the organic material in which:
  a) The solid feedstock is subjected to a gasification stage so as to convert said feedstock into synthesis gas comprising carbon monoxide and hydrogen,
  b) the synthesis gas that is obtained in stage a) is subjected to a purification treatment that comprises an adjustment for increasing the molar ratio of hydrogen to carbon monoxide, $H_2/CO$, up to a predetermined value, preferably between 1.8 and 2.2,
  c) the purified synthesis gas that is obtained in stage b) is subjected to a conversion stage that comprises the implementation of a Fischer-Tropsch-type synthesis so as to convert said synthesis gas into a liquid effluent and a gaseous effluent,
  d) the liquid effluent that is obtained in stage c) is fractionated so as to obtain at least two fractions that are selected from the group that consists of: a gaseous fraction, a naphtha fraction, a kerosene fraction, and a gas oil fraction, and
  e) at least a portion of the naphtha fraction is recycled in gasification stage."

The naphtha recycle stream that is generated in this process is introduced into the gasification stage. To introduce the naphtha to the gasification stage as taught in Bayle et al., is to modify the $H_2/CO$ ratio in the gasification stage using an oxidizing agent such as water vapour and gaseous hydrocarbon feedstocks such as natural gas with the recycled naphtha, while maximizing the mass rate of carbon monoxide and maintain sufficient temperature above 1000° C. to 1500° C. in the gasification stage to maximize the conversion of tars and light hydrocarbons.

U.S. Pat. No. 6,696,501 (Schanke et al.) entitled Optimum Integration Process for Fischer-Tropsch Synthesis and Syngas Production discloses a process for the conversion of natural gas or other fossil fuels to higher hydrocarbons. In the process disclosed therein the natural gas or the fossil fuels is reacted with steam and oxygenic gas in a reforming zone to produce synthesis gas which primarily contains hydrogen, carbon monoxide and carbon dioxide. The synthesis gas is then passed into a Fischer-Tropsch reactor to produce a crude synthesis containing lower hydrocarbons, water and non-converted synthesis gas. Subsequently, the crude synthesis stream is separated in a recovery zone into a crude product stream containing heavier hydrocarbons, a water stream and a tail gas stream containing the remaining constituents. It is also taught that the tail gas stream is reformed in a separate steam reformer with steam and natural gas and then the sole reformed tail gas is introduced into the gas stream before being fed into the Fischer-Tropsch reactor.

In this reference, a high carbon dioxide stream is recycled back to an ATR in order to maximize the efficiency of the carbon in the process. It is further taught that the primary purpose of reforming and recycling the tail gas is to steam reform the lower hydrocarbons to carbon monoxide and hydrogen and as there is little in the way of light hydrocarbons, adding natural gas will therefore increase the carbon efficiency. In the Schanke et al. reference, the patentees primarily focused on the production of the high carbon content syngas in a GTL environment using an ATR as crude synthesis stream and reforming the synthesis tail gas in an SMR with natural gas addition to create optimum conditions that feed to the Fischer-Tropsch reactor.

In respect of other progress that has been made in this field of technology, the art is replete with significant advances in, not only gasification of solid carbon feeds, but also methodology for the preparation of syngas, management of hydrogen and carbon monoxide in a GTL plant, the Fischer-Tropsch reactors management of hydrogen, and the conversion of biomass feedstock into hydrocarbon liquid transportation fuels, inter alia. The following is a representative list of other such references. This includes: U.S. Pat. Nos. 7,776,114; 6,765,025; 6,512,018; 6,147,126; 6,133,328; 7,855,235; 7,846,979; 6,147,126; 7,004,985; 6,048,449; 7,208,530; 6,730,285; 6,872,753, as well as United States Patent Application Publication Nos. US2010/0113624; US2004/0181313; US2010/0036181; US2010/0216898; US2008/0021122; US 2008/0115415; and US 2010/0000153.

U.S. Pat. No. 7,168,265 discloses an integrated process for producing LNG and GTL products, wherein a $CO_2$-containing natural gas feed to an LNG production zone is first pretreated to separate at least a portion of the $CO_2$ therefrom, and the resulting $CO_2$ stream obtained thereby is then directed to a GTL production zone and utilized to make GTL products that include methanol and/or methanol derivatives.

Applicant's co-pending application Ser. No. 13/228,042 provides a process for synthesizing hydrocarbons, comprising: a) formulating a hydrogen rich stream with a syngas generator; b) catalytically converting said stream to produce hydrocarbons, containing at least naphtha; c) recycling at least a portion of said naphtha to said syngas generator to form an enhanced hydrogen rich stream; and d) re-circulating said enhanced hydrogen rich stream from step (c) for conversion in step (b) to enhance the synthesis of hydrocarbons.

Although the processes disclosed in U.S. Ser. No. 13/228,042 allow for the conversion of greater than 65% of all carbon in the feed streams to hydrocarbon products, and the process disclosed in U.S. Pat. No. 7,168,265 allow for co-production of methanol, there remains a need for technology that provides for an optimized conversion of the unconverted process $CO_2$ and other by-products of the hydrocarbon production process to commercially valuable co-products such that 100% of all the carbon in captured $CO_2$ by-product streams can be converted to valuable commercial co-products.

As part of the further advancements set forth herein, there are provided processes for the optimized production of commercially useful co-products from the by-products of the hydrocarbon synthesis process. These processes can be integrated within hydrocarbon synthesis systems as described, for example, in co-pending U.S. Ser. No. 13/228,042.

SUMMARY OF THE INVENTION

One object of the present invention is to provide an improved Fischer-Tropsch based synthesis process for synthesizing hydrocarbons with a substantially increased yield.

A further object of one embodiment of the present invention is to provide a process for co-producing commercially valuable products from by-products of a process for synthesizing hydrocarbons, comprising the steps of:
(a) formulating a first hydrogen rich syngas stream with a syngas generator;
(b) subjecting a portion of said first hydrogen rich syngas stream to a hydrogen separator unit to provide a purified hydrogen by-product stream and a second hydrogen rich syngas stream;
(c) subjecting at least a portion of said first hydrogen rich syngas stream, at least a portion of said second hydrogen rich syngas stream, or a combination thereof, to a carbon dioxide removal operation to obtain purified hydrogen rich syngas stream and a carbon dioxide by-product stream;
(d) catalytically converting said purified hydrogen rich syngas stream to synthesize said hydrocarbons; and
(e) converting said purified hydrogen by-product stream and/or said carbon dioxide by-product stream into said commercially valuable co-products.

The present invention amalgamates a series of known unit operations into a much improved synthesis route for production of synthetic hydrocarbon fuels and co-production of commercially valuable co-products from by-products of this synthetic route.

In accordance with an embodiment of the instant methodology, the process may include an autothermal reforming unit (ATR) operation as a syngas generator. As is well known to those skilled in the art, autothermal reforming employs oxygen and carbon dioxide and or steam, in a reaction with light hydrocarbon gases like natural gas to form syngas. This is an exothermic reaction in view of the oxidation procedure. When the autothermal reformer employs carbon dioxide, the hydrogen to carbon monoxide ratio produced is 1:1 and when the autothermal reformer uses steam, the ratio produced is approximately 2.5:1. One of the more significant benefits of using the ATR is realized in the variability of the hydrogen to carbon monoxide ratio.

The reactions that are incorporated in the autothermal reformer are as follows:

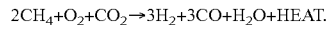

When steam is employed, the reaction equation is as follows:

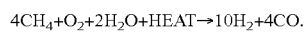

In accordance with a further embodiment of the instant methodology, the process may include a steam methane reformer (SMR) operation as a syngas generator. As is well known to those skilled in the art, steam methane reforming employs steam in a reaction with light hydrocarbon gases like natural gas and pre-reformed ethane, propane, butane and or naphtha to form syngas in an indirect fired heater configuration. This is an endothermic reaction where external heat energy is required to support the reaction.

The primary reaction that is incorporated in the steam methane reformer is as follows:

$$\text{Natural Gas} + \text{Steam} + \text{Heat} \rightarrow CO + nH_2 + CO_2.$$

With the steam methane reformer, the hydrogen to carbon monoxide ratio produced ranges from 3:1 to 6:1. One of the more significant benefits of using the SMR is realized in the capability of generating relatively high hydrogen to carbon monoxide ratios, particularly attractive where excess hydrogen is needed for other operations, such as for the synthetic hydrocarbon upgrading or other co-product as described by the current invention.

A further discovery materialized from making use of, for example, light hydrocarbon gas as by-product from the Fischer-Tropsch reaction and hydrocarbon upgrader processing, commonly known as FT Tailgas and Upgrader offgases, or combined to form a refinery fuel gas, as a recycled feedstock to the ATR, SMR or combination thereof together with the naphtha recycle feedstock, resulted in a significant increase in the volume of syndiesel fuel produced. By way of example, by employing the combination of SMR and ATR with naphtha recycle, and the recycled refinery fuel gases, the process is capable of converting at least 50% or greater of all the carbon introduced to the process to syndiesel with an increase in production of syndiesel and synthetic jet fuel, as compared to conventional Fischer-Tropsch operation and without the production of any hydrocarbon by-products. This obviously has significant economic benefits.

The present invention amalgamates previously unrecognized combinations in a hydrocarbon synthesis process, in particular Fischer-Tropsch based process for synthesizing hydrocarbons, which expands the usefulness of these processes, by providing a number of integrated strategies which are not available in stand-alone synthesis plants. In the process of the present application, in addition to the production of synthetic diesel and synthetic jet streams, it is possible to optimally convert excess or by-product $CO_2$, nitrogen ($N_2$) and hydrogen ($H_2$) to commercially valuable co-products.

Referring now to the drawings as they generally describe the invention, reference will now be made to the accompanying drawings illustrating preferred embodiments.

BRIEF DESCRIPTION OF THE DRAWINGS

The dashed lines used in the Figures denote optional operations.

Similar numerals employed in the figures denote similar elements.

DETAILED DESCRIPTION OF THE PREFERRED EMBODIMENTS

Figure 1:
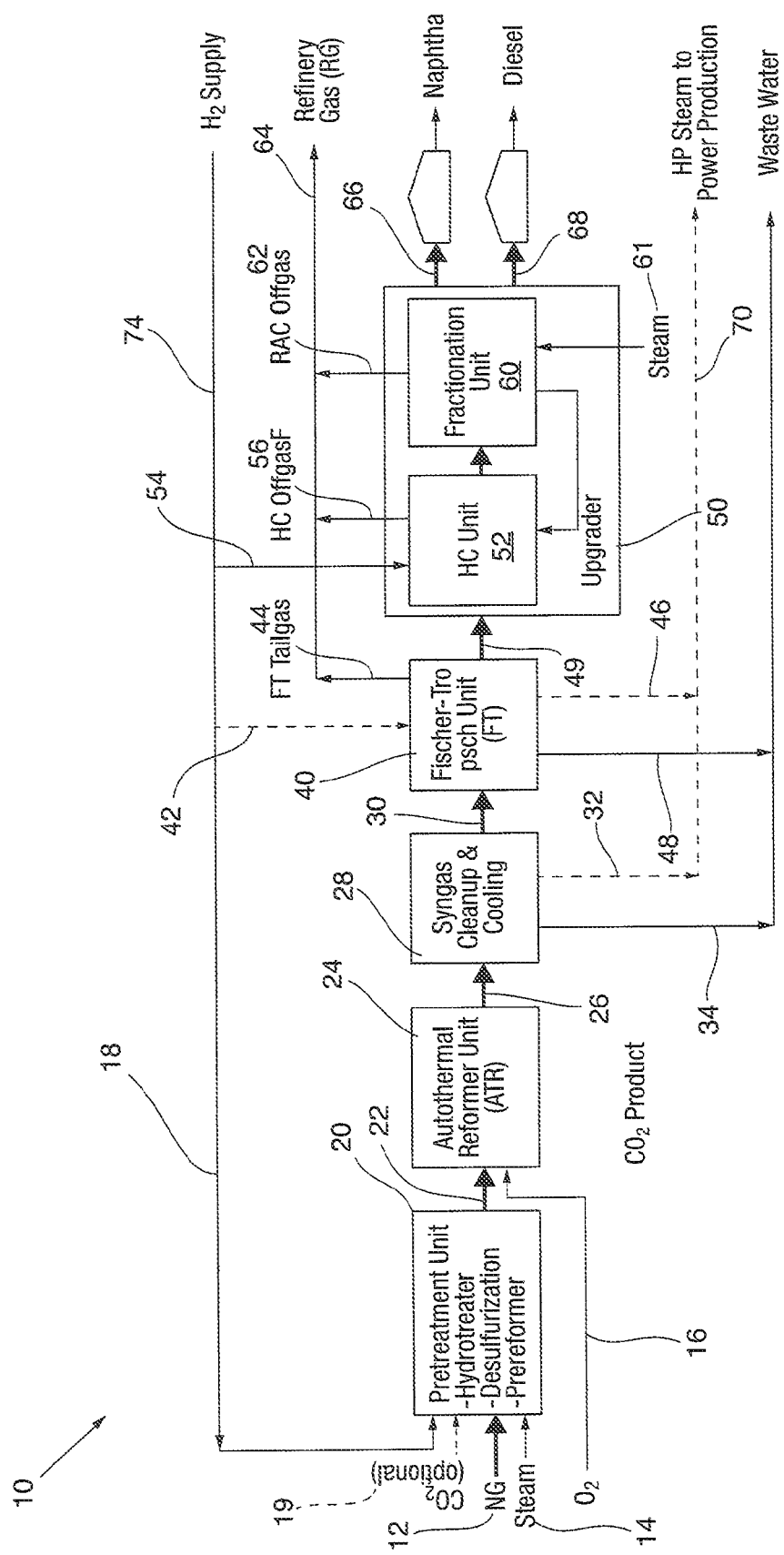
FIG. 1 is a process flow diagram of methodology known in the prior art using autothermal reformer technology.

Referring now to FIG. 1, to illustrate prior art, shown is a process flow diagram of a circuit for converting gas-to-liquids with the result being the production of naphtha and syndiesel. The process is generally denoted by numeral 10 and begins with a natural gas supply 12, which feedstock can be in the form of raw field gas or pipeline quality treated gas, usually with bulk sulfur and hydrocarbon liquids removed. The natural gas is then pre-treated in a pre-treatment unit 20 to which steam 14, hydrogen 18 and optionally carbon dioxide 19 may be added as required. The pre-treatment unit may include, as is well known to those skilled in the art, such unit operations as a feed gas hydrotreater, sulfur removal and guard operation and a pre-reformer to produce a clean vapour feed stream 22 for the syngas generator, denoted in FIG. 1 as an autothermal reformer (ATR) unit 24. The ATR 24 may be any suitable catalytic partial oxidization unit, however, as an example; an ATR that is useful in this process is that of HaldorTopsoe A/S., Uhde GmbH and CB&I Lummus Company. The ATR process and apparatus have been found to be effective in the methodology of the present invention and will be discussed hereinafter.

Generally, as is known from the ATR process, the same effectively involves a thermal catalytic stage which uses an partial oxygen supply 16 to convert the preconditioned natural gas feed to a syngas 26 containing primarily hydrogen and carbon monoxide.

The so formed syngas is then subjected to cooling and cleaning operations 28 with subsequent production of steam 32 and removal of produced water at 34. Common practice in the prior art is to employ the use of a water gas shift reaction (WGS) on the clean syngas 30 to condition the hydrogen to carbon dioxide ratio to near 2.0:1 for optimum conditions for the Fischer-Tropsch unit 40. It is not preferred in this process to include a WGS reaction as all the carbon, primarily as CO is used to maximize production of synthesis liquids product. The process may optionally use the supplemental addition of hydrogen 42 to maximize the conversion to syndiesel. The raw syngas may be further treated, as is well known to those skilled in the art, in various steps of scrubbing units and guard units to remove ammonia and sulfur compounds to create a relatively pure clean syngas 30 suitable for use in a Fischer-Tropsch unit. A carbon dioxide removal unit (not shown) may optionally be included in the clean syngas stream 30 to reduce the inert load and maximize the carbon monoxide concentration to the Fischer-Tropsch unit 40. The syngas is then transferred to a Fischer-Tropsch reactor 40 to produce the hydrocarbons 49 and water 48. The so formed hydrocarbons are then passed on to a product upgrader, generally denoted as 50, and commonly including a hydrocarbon cracking stage 52, a product fractionating stage 60 with naphtha being produced at 66 as a fraction, as well as diesel 68 as an additional product. The diesel 68 formulated in this process is commonly known as syndiesel. As an example, this process results in the formulation of 1000 barrels per day (bbl/day) based on 10 to 15 million standard cubic feet/day (MMSCFD) of natural gas. As is illustrated in the flow diagram, a source of hydrogen 74 is to be supplemented to the hydrocarbon cracking unit 52 denoted as streams 54. Further, energy 32 from the syngas generator 24, typically in the form of steam, may be used to generate power and this is equally true of the Fischer-Tropsch reactor 40 creating energy 46.

Table 1 establishes a comparison between FT diesel and conventional petroleum based diesel.

TABLE 1

Specification of FT-Diesel in Comparison to Conventional Diesel

| Diesel Fuel Specification | FT-Diesel | Conventional Diesel |
|---|---|---|
| Chemical formula | Paraffin | $C_{12}H_{26}$ |
| Molecular weight (kg/kmol) | | 170-200 |
| Cetane number | >74 | 50 |
| Density (kg/l) at 15° C. | 0.78 | 0.84 |
| Lower heating value (MJ/kg) at 15° C. | 44.0 | 42.7 |
| Lower heating value (MJ/l) at 15° C. | 34.3 | 35.7 |
| Stoichiometric air/fuel ratio (kg air/kg fuel) | | 14.53 |
| Oxygen content (% wt) | ~0 | 0-0.6 |
| Kinematic viscosity ($mm^2$/s) at 20° C. | 3.57 | 4 |
| Flash point (° C.) | 72 | 77 |

Source: KMITL Sci. Tech. J. Vol. 6 No. 1 January-June 2006, p. 43

As a further benefit, known to those skilled in the art, the process as described by FIG. 1 and all configurations of the current invention, the addition of a further side stripper column (not shown) off the fractionation in stage 60 may be included to produce a new fraction of about 25% of the volume of the syndiesel fuel (200 to 300 barrels per day (bbl/day)), referred to as FT-jet fuel. Table 2 describes a typical characteristic of FT jet fuel.

TABLE 2

Typical Specification of FT-Jet Fuel

| Typical Product Specification | FT Jet Fuel |
|---|---|
| Acidity mg KOH/g | 0.10 |
| Aromatics % vol max | <25.0 |
| Sulfur mass % | <0.40 |
| Distillation ° C. | Min 125° C. max 190° C. |
| 50% recovered End Point | 270° C. |
| Vapor Pressure kPa max | 21 |
| Flash Point ° C. | — |
| Density 15° C., kg/m3 | 750-801 |
| Freezing Point ° C. max | −51 |
| Net Heat Combustion MJ/kg min | 42.8 |
| Smoke Point mm, min | 20 |
| Naphthalenesvol % max | <3.0 |
| Copper Corrosion 2 hr @ 100° C., max rating | No 1 |
| Thermal Stability | |
| Filter Pressure drop mm Hg, max | 25 |
| Visual Tube rating, max | <3 |
| Static Test 4 hr @ 150° C. mg/100 ml, max | |
| Existent Gum mg/100 ml, max | |

Naphtha 66 can be generally defined as a distilled fraction of the Fischer-Tropsch FT hydrocarbon liquids, categorized by way of example with a typical boiling range of 30° C. to 200° C., and more preferred 80° C. to 120° C. The specific naphtha specification will be optimized for each application to maximize syndiesel production, maximize the recovery of light liquid hydrocarbon fractions such as propane and butane and partially or fully eliminate the naphtha by-product.

Suitable examples of FT reactors include fixed bed reactors, such as tubular reactors, and multiphase reactors with a stationary catalyst phase and slurry-bubble reactors. In a fixed bed reactor, the FT catalyst is held in a fixed bed contained in tubes or vessels within the reactor vessel. The syngas flowing through the reactor vessel contacts the FT catalyst contained in the fixed bed. The reaction heat is removed by passing a cooling medium around the tubes or vessels that contain the fixed bed. For the slurry-bubble reactor, the FT catalyst particles are suspended in a liquid, e.g., molten hydrocarbon wax, by the motion of bubbles of syngas sparged into the bottom of the reactor. As gas bubbles rise through the reactor, the syngas is absorbed into the liquid and diffuses to the catalyst for conversion to hydrocarbons. Gaseous products and unconverted syngas enter the gas bubbles and are collected at the top of the reactor. Liquid products are recovered from the suspending liquid using different techniques such as separators, filtration, settling, hydrocyclones, and magnetic techniques. Cooling coils immersed in the slurry remove heat generated by the reaction. Other possibilities for the reactor will be appreciated by those skilled.

In the FT process, $H_2$ and CO combine via polymerization to form hydrocarbon compounds having varying numbers of carbon atoms. Typically 70% conversion of syngas to FT liquids takes place in a single pass of the FT reactor unit. It is also common practice to arrange the multiple FT reactors in series and parallel to achieve conversion levels of 90+%. A supplemental supply of hydrogen 42 may be provided to each subsequent FT reactor stages to enhance the conversion performance of the subsequent FT stages. After the FT reactor, products are sent to the separation stage, to divert the unconverted syngas and light hydrocarbons (referred to as FT tailgas), FT water and the FT liquids, which are directed to the hydrocarbon upgrader unit denoted as 50. The FT tailgas becomes the feed Stream for subsequent FT stages or is directed to refinery fuel gas 64 in the final FT stage. The upgrader unit typically contains a hydrocracking step 52 and a fractionation step 60.

Hydrocracking denoted as 52 used herein is referencing the splitting an organic molecule and adding hydrogen to the resulting molecular fragments to form multiple smaller hydrocarbons (e.g., $C_{10}H_{22}+H_2 \rightarrow C_4H_{10}$ and skeletal isomers+$C_6H_{14}$). Since a hydrocracking catalyst may be active in hydroisomerization, skeletal isomerization can occur during the hydrocracking step. Accordingly, isomers of the smaller hydrocarbons may be formed. Hydrocracking a hydrocarbon stream derived from Fischer-Tropsch synthesis preferably takes place over a hydrocracking catalyst comprising a noble metal or at least one base metal, such as platinum, cobalt-molybdenum, cobalt-tungsten, nickel-molybdenum, or nickel-tungsten, at a temperature of from about 550° F. to about 750° F. (from about 288° C. to about 400° C.) and at a hydrogen partial pressure of about 500 psia to about 1,500 psia (about 3,400 kPa to about 10,400 kPa).

The hydrocarbons recovered from the hydrocracker are further fractionated in the fractionation unit 60 and refined to contain materials that can be used as components of mixtures known in the art such as naphtha, diesel, kerosene, jet fuel, lube oil, and wax. The combined unit consisting of the hydrocracker 52 and hydrocarbon fractionator 60 are commonly known as the hydrocarbon upgrader 50. As is known by those skilled in the art, several hydrocarbon treatment methods can form part of the upgrader unit depending on the desired refined products, such as additional hydrotreating or hydroisomerization steps. The hydrocarbon products are essentially free of sulfur. The diesel may be used to produce environmentally friendly, sulfur-free fuel and/or blending stock for diesel fuels by using as is or blending with higher sulfur fuels created from petroleum sources.

Unconverted vapour streams, rich in hydrogen and carbon monoxide and commonly containing inert compounds such as carbon dioxide, nitrogen and argon are vented from the process as FT tail gas 44, hydrocracker (HC) offgas 56 and fractionator (frac) offgas 62. These streams can be commonly collected as refinery fuel gas 64 and used as fuel for furnaces and boilers to offset the external need for natural gas. These streams may also be separated and disposed of separately based on their unique compositions, well known to those skilled in the art.

A supplemental supply of hydrogen 74 may be required for the HC unit 54 and the natural gas hydrotreater 18. This hydrogen supply can be externally generated or optionally provided from the syngas stream 30 using a pressure swing absorption or membrane unit (not shown), although this feature will increase the volume of syngas required to be generated by the syngas generator 24.

Further, useable energy commonly generated as steam from the syngas stage, denoted by numeral 32, may be used to generate electric power 70. This is equally true of useable energy that can be drawn from the Fischer-Tropsch unit, owing to the fact that the reaction is very exothermic and this represents a useable source of energy. This is denoted by numeral 46.

Figure 2:
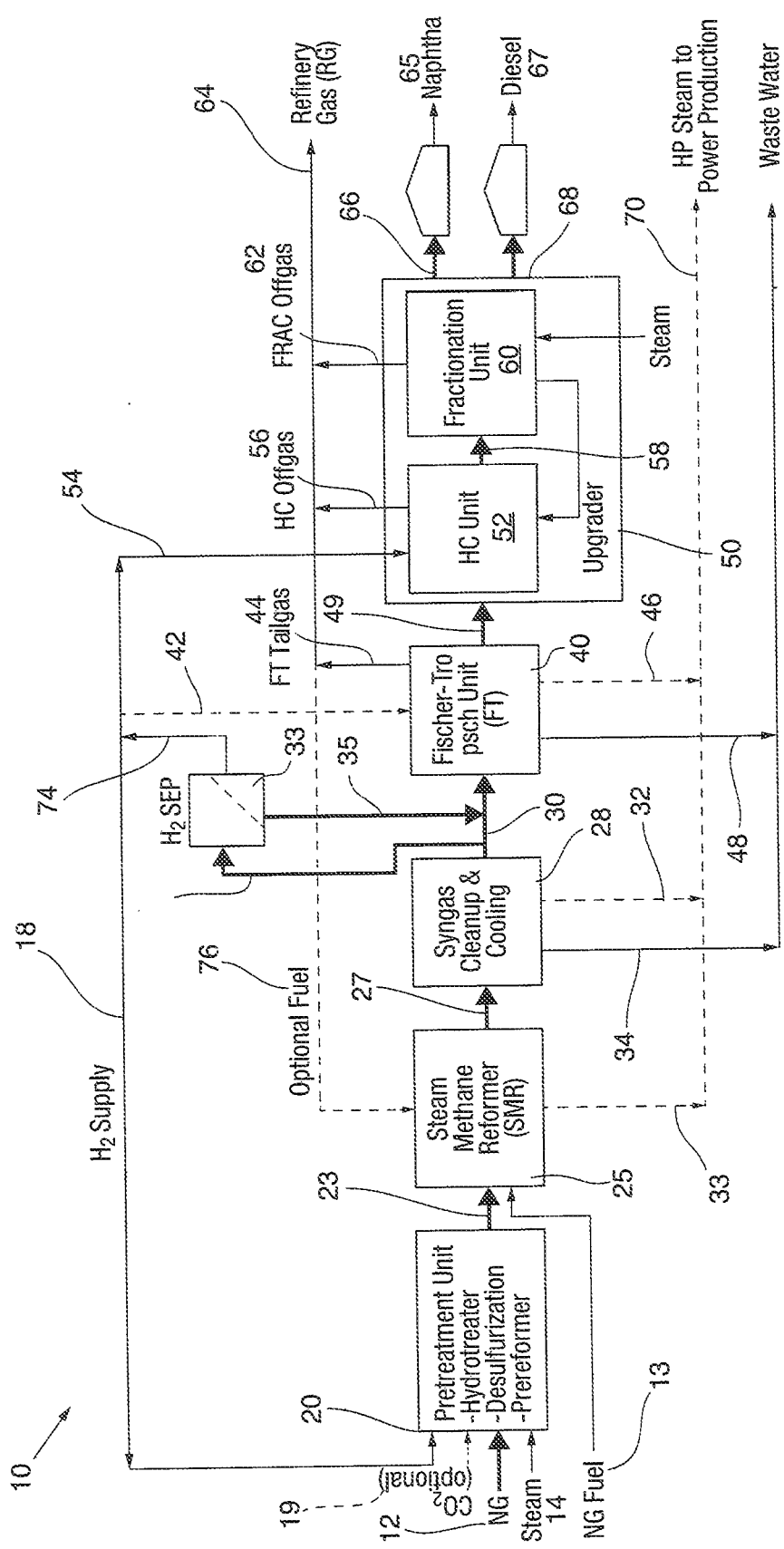
FIG. 2 is a process flow diagram of methodology known in the prior art using steam methane reformer technology.

Referring now to FIG. 2, to further illustrate the prior art, shown is an alternate process flow diagram of a circuit for converting gas-to-liquids with the result being the production of naphtha and syndiesel. The components of this process are generally the same as that described in FIG. 1 with the common elements denoted with the same numbers. For this process, the syngas generator is changed to be a steam methane reformer (SMR) 25. The SMR 25 may be any suitable catalytic conversion unit, however, as an example, an SMR that is useful in this process is that of HaldorTopsoe A/S., Uhde GmbH., CB&I Lummus Company, Lurgi GmbH/Air LiquideGruppe, TechnipInc, Foster Wheeler and others. The SMR process and apparatus have been found to be effective in executing the methodology of the present invention to be discussed hereinafter. Generally, as is known from the SMR process, the same effectively involves a thermal catalytic stage which uses steam supply and heat energy to convert the preconditioned natural gas feed to a syngas 27 containing primarily hydrogen and carbon dioxide.

An advantage of the SMR technology is that the syngas is very rich in hydrogen with a ratio of hydrogen to carbon monoxide typically greater than 3.0:1. This exceeds the typical syngas ratio of 2.0:1 usually preferred for the Fischer-Tropsch process. As such, a hydrogen separation unit 33 may be used to provide the hydrogen requirement 74 for the GTL process. As discussed previously, well known to those skilled in the art, the hydrogen separator may be a pressure swing adsorption, an absorption unit and or a membrane separation unit or any combination. A water gas shift reaction may also be optionally installed ahead of the hydrogen separator. Further, although the SMR does not require an oxygen source as with the ATR technology, the SMR process requires external heat energy, typically provided by natural gas 13 or optionally by use of the excess refinery gas 76 and 104 derived from the FT tail gas 44 or upgrader offgases 56 & 62.

The SMR 25 may contain any suitable catalyst and be operated at any suitable conditions to promote the conversion of the hydrocarbon to hydrogen ($H_2$) and carbon monoxide (CO). The addition of steam and natural gas may be optimized to suit the desired production of hydrogen and carbon monoxide. Generally natural gas or any other suitable fuel can be used to provide energy to the SMR reaction furnace. The catalyst employed for the steam reforming process may include one or more catalytically active components such as palladium, platinum, rhodium, iridium, osmium, ruthenium, nickel, chromium, cobalt, cerium, lanthanum, or mixtures thereof. The catalytically active component may be supported on a ceramic pellet or a refractory metal oxide. Other forms will be readily apparent to those skilled.

Figure 3:
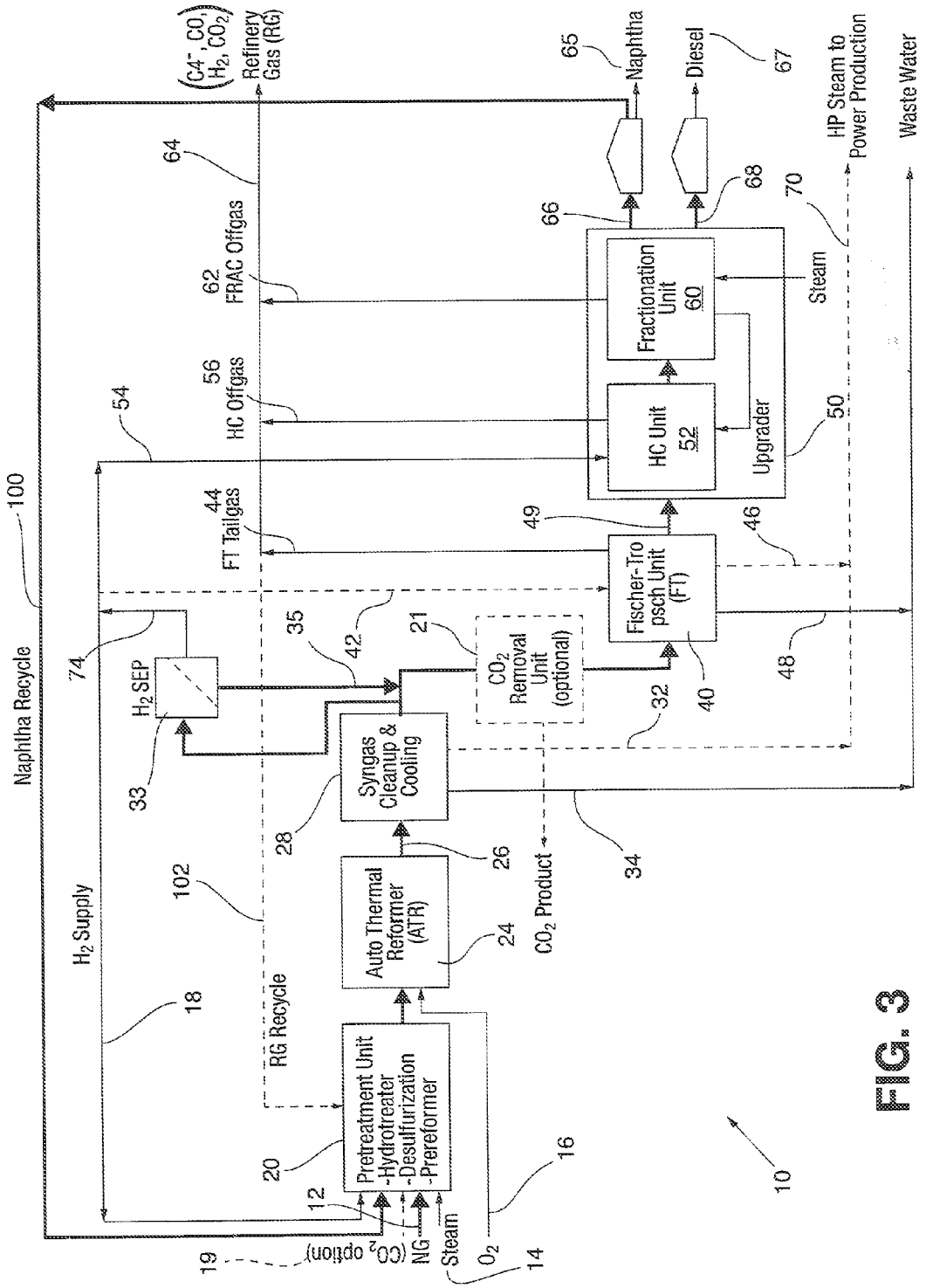
FIG. 3 is a process flow illustrating another methodology of hydrocarbon synthesis process in a GTL environment.

FIG. 3, depicts an embodiment of the technology described in the co-pending application Ser. No. 13/228,042. Many of the preliminary steps of the process described in FIG. 3 are common with the process depicted in FIG. 1. At least a portion of the less desirable FT product, naphtha 66 is recycled as ATR 24 feed through the pre-treatment unit 20 and is fully destroyed and converted to additional syngas. Based on the full recycle and conversion of the naphtha, the diesel production increase of greater than 10% can be realized, with the elimination of an undesirable by-product hydrocarbon stream.

In the embodiment shown in FIG. 3, several other optional features are desirable in addition to naphtha recycle, to enhance the production of syndiesel, including; (i) a hydrogen separation unit is added to remove excess hydrogen from the enhanced syngas for supply to the FT unit 40 and product upgrades 50; (ii) A portion of hydrogen rich streams not desired to be used as fuel, separately or combined all together as refinery fuel 64, can be recycled back 102 to the ATR 24 by way of the pre-treatment unit 20; (iii) A optional carbon dioxide removal stage 21 may be installed on the FT syngas feedstream to reduce the inert vapour load on the FT unit 40, and at least a portion of the carbon dioxide 12 may be reintroduced into the ATR 24 by way of the pre-treatment unit 20 for purposes of reverse shifting and recycling carbon to enhance the production of syndiesel.

Figure 4:
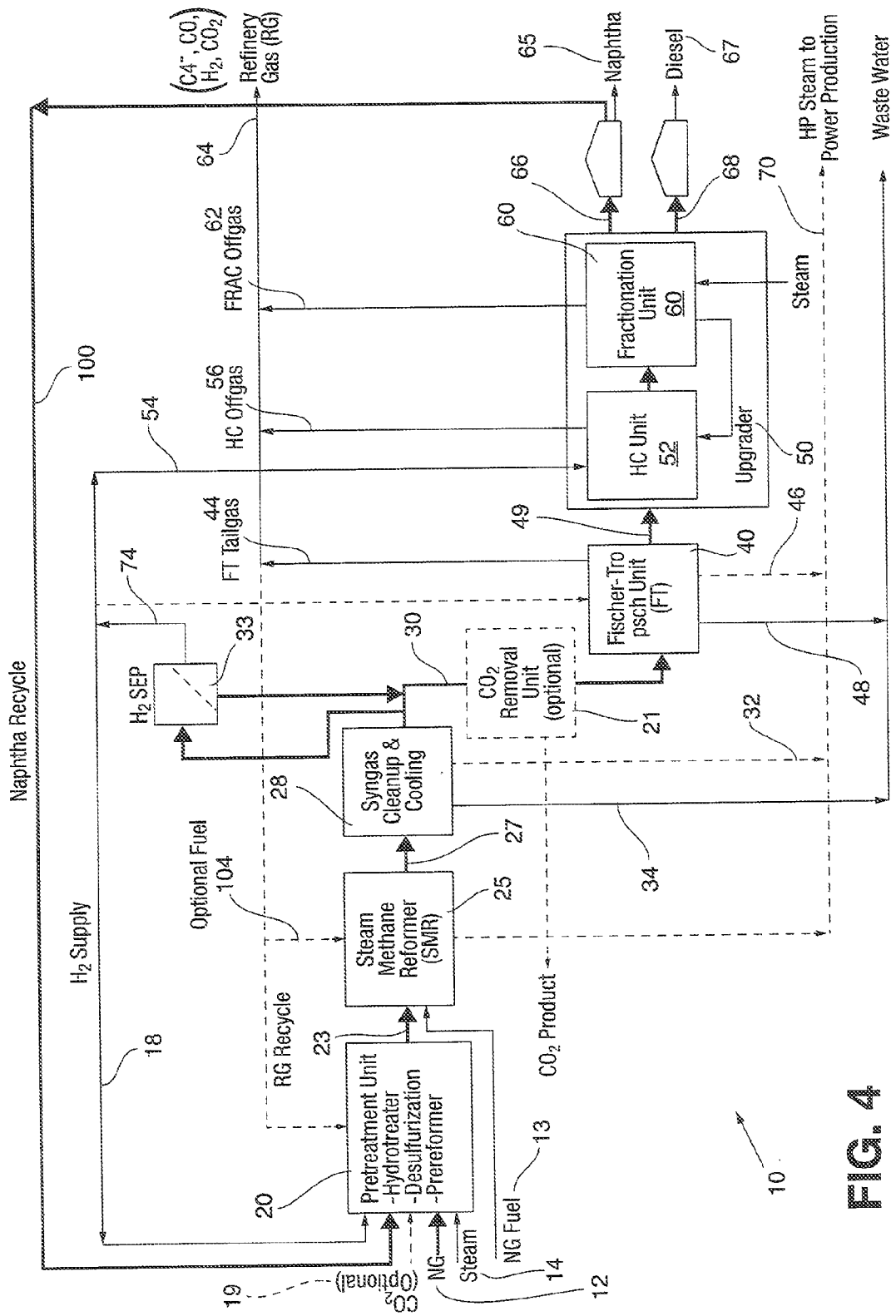
FIG. 4 is a process flow diagram illustrating a further variation of the methodology of hydrocarbon synthesis process in a GTL environment illustrated in FIG. 3.

FIG. 4 sets forth a further variation on the overall process that is set forth in FIG. 3. As is evinced from FIG. 4, many of the preliminary steps are common with that which is shown in FIG. 2. In this variation, and similar to the variation described by FIG. 3, the process employs the recycle of at least a portion of the naphtha 100 to enhance the production of syndiesel using a SMR syngas generator. Similarly the optional features described for FIG. 3 can equally apply to FIG. 4.

Figure 5:
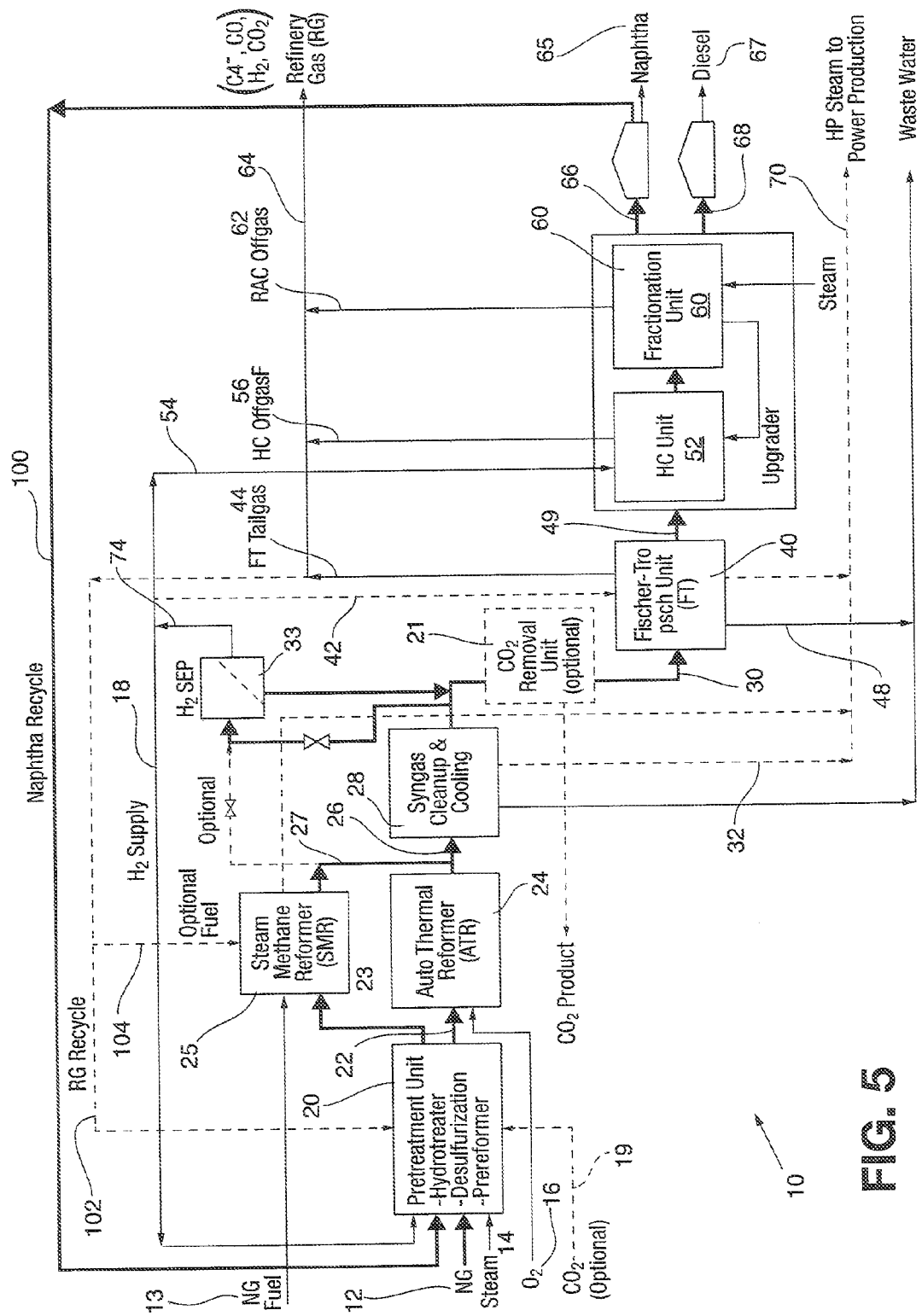
FIG. 5 is a process flow diagram of a still further variation of the methodology of FIGS. 3 and 4 showing the combination of autothermal and steam methane reforming technologies.

A further variation of the overall process embraced by the technology discussed in the co-pending application Ser. No. 13/228,042 is shown in FIG. 5. In essence, the process flow as shown in FIG. 5 combines the unit operations of the SMR 25 and the ATR 24 syngas generators with the primary embodiment of this invention, namely the recycle of at least a portion of the naphtha, to create the maximum conversion of carbon to syndiesel. Further, the optional features as described in FIGS. 3 and 4, combined with the naphtha recycle, may create even further benefits to further enhancement of syndiesel production without any nonuseful by-products. The sizing of the ATR and SMR syngas generators are specific to each feed gas compositions and site specific parameters to optimize the production of syndiesel. Further the feedstreams for the ATR and SMR may be common or uniquely prepared in the pretreatment unit to meet specific syngas compositions desired at 26 and 27. Similarly, the hydrogen rich syngas stream or portion thereof, from the SMR can be optionally preferred as the feed stream to the hydrogen separation unit 33. By way of example, the preferred steam to carbon ratios at streams 22 and 23 for the ATR and SMR may be different, thereby requiring separate pre-treatment steps.

Figure 6:
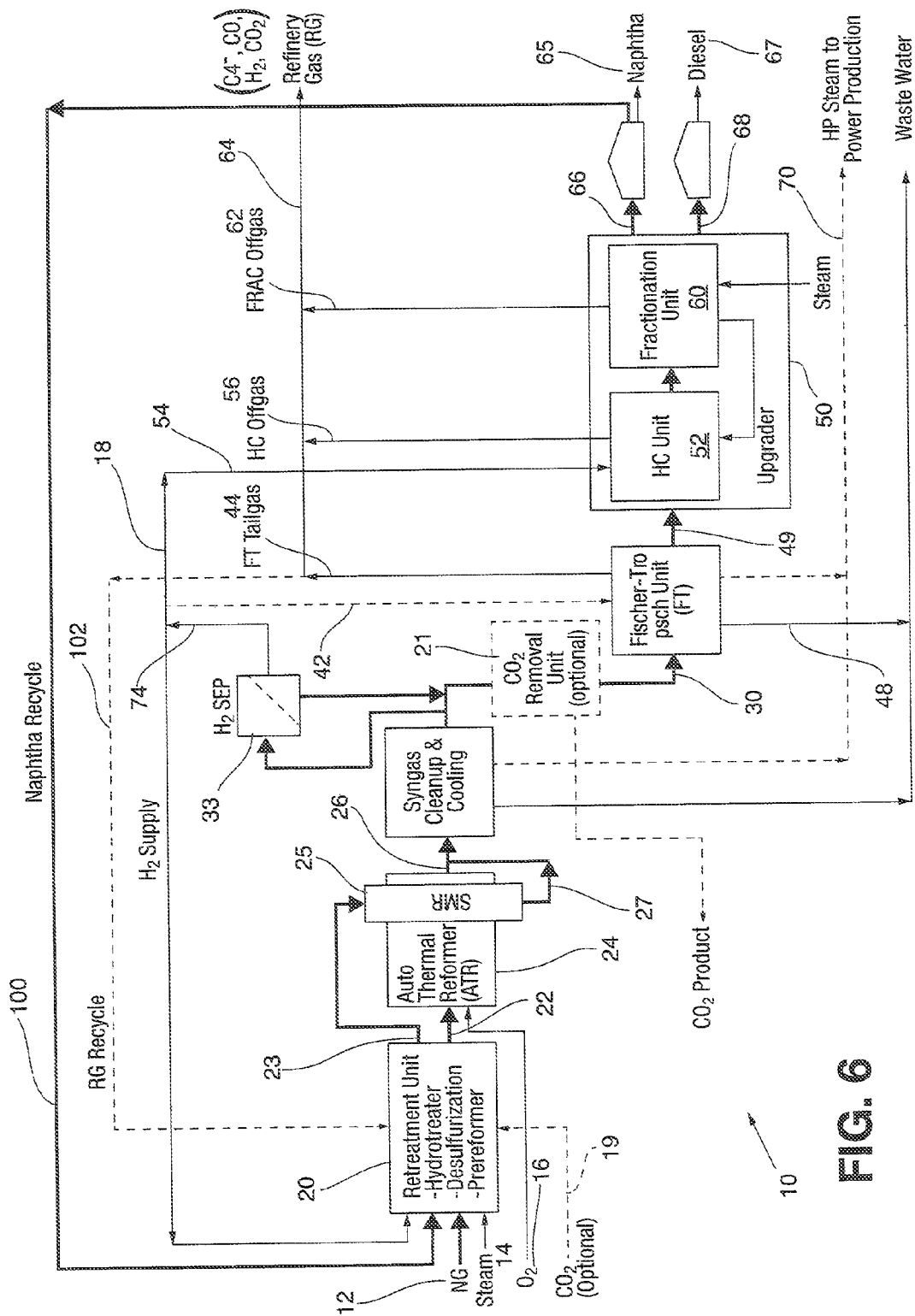
FIG. 6 is a process flow diagram illustrating a still further variation of the process of FIGS. 3 and 4, showing the integration of the autothermal and steam methane technologies.

Turning to FIG. 6, as shown is yet another variation of the overall process disclosed in the co-pending application Ser. No. 13/228,042 combining the benefits of FIGS. 3 and 4. In this embodiment, both the SMR and ATR unit operations, combined with the naphtha recycle are amalgamated into an integrated unit operation whereby the heat energy created by the ATR 24 becomes the indirect heat energy required by the SMR reactor tubes 25. This embodiment allows the integrated ATR/SMR unit, the XTR to be strategically designed to maximize the carbon conversion to syndiesel by creating the optimum Fischer-Tropsch 40 and hydrogen separator 33 syngas feed with optimum hydrogen to carbon monoxide ratio and the minimum quantity of natural gas, steam and oxygen, while maximizing syndiesel production without the production of any non-useful hydrocarbon by-product. All other optional features remain the same as FIGS. 3, 4 and 5. As used herein, "integrated" in reference to the ATR/SMR means a merged unit where the two distinct operations are merged into one.

The hydrocarbon synthesis processes described in prior art and in the co-pending application Ser. No. 13/228,042 are very efficient in retaining and managing carbon, and can produce a very high yield synthetic hydrocarbon products while converting greater than 60% of the carbon in the feed streams, and more preferred greater than about 70% of the carbon in the feed streams. The unconverted carbon (about 30%) can be captured and commercially sold for commercial use or for enhanced oil recovery, or less preferred, but more typically sequestered or discharged to atmosphere as Green House Gases (GHG). The present invention provides a means for converting the by-product $CO_2$ into commercially valuable co-products in an optimal manner. One embodiment of the present invention is to integrate a methanol ($CH_3OH$) synthesis unit to use all of the excess process and combustion derived $CO_2$ and any externally available $CO_2$, through reaction with portions of hydrogen rich syngas and purified hydrogen ($H_2$), in the production of these commercially valuable co-products.

In the hydrocarbon synthesis processes described herein and in the co-pending application Ser. No. 13/228,042, oxygen may be used in the ATR or POX syngas generator. In one embodiment, an oxygen plant (ASU—Air Separation Unit) is used to separate air into near pure oxygen $O_2$ and near pure nitrogen ($N_2$) streams. This $N_2$ is typically partially or entirely vented to atmosphere if there is no commercial or process unit use. A further embodiment of the present invention is to integrate an ammonia ($NH_3$) synthesis unit to convert the excess $N_2$ into ammonia through reaction with purified hydrogen stream $H_2$. In another embodiment of the present invention, a portion of the ammonia is further converted to urea by reaction with by-product $CO_2$ in a urea synthesis unit.

The hydrocarbon synthesis process described herein and in the co-pending application Ser. No. 13/228,042 uses a rich hydrogen syngas from a syngas generator to feed an optimum $H_2$:CO ratio of 1.8 to 2.1, more preferred ratio of 2.0 to Fischer Tropsch (FT) Synthesis Unit. Simultaneously purified hydrogen ($H_2$) by-product is produced from the Syngas Generators for synthetic hydrocarbon upgrading use. Both the rich hydrogen syngas stream and purified hydrogen streams can be used coincidental base feed streams for the methanol and ammonia co-production discussed above.

Common hydrocarbon synthesis process units, such as Syngas Generators, including Steam Methane Reformers (SMR), Auto-Thermal Reformers (ATR), Partial Oxidation Units (POX) or combinations of above units can be used for the base hydrocarbon synthesis complex and integrated for use as co-production syngas generator or hydrogen units for Ammonia and Methanol synthesis. The incremental increase in unit capacities provide economies of scale co-production that support lowest cost production.

In the process of the present invention near 100% of all the by-product $CO_2$ streams captured from the hydrocarbon production as unconverted carbon streams, fuel gas streams and flue gas streams from combustion systems (i.e. furnaces, boilers, power generators) can be converted to valuable commercial co-products.

Figure 7:
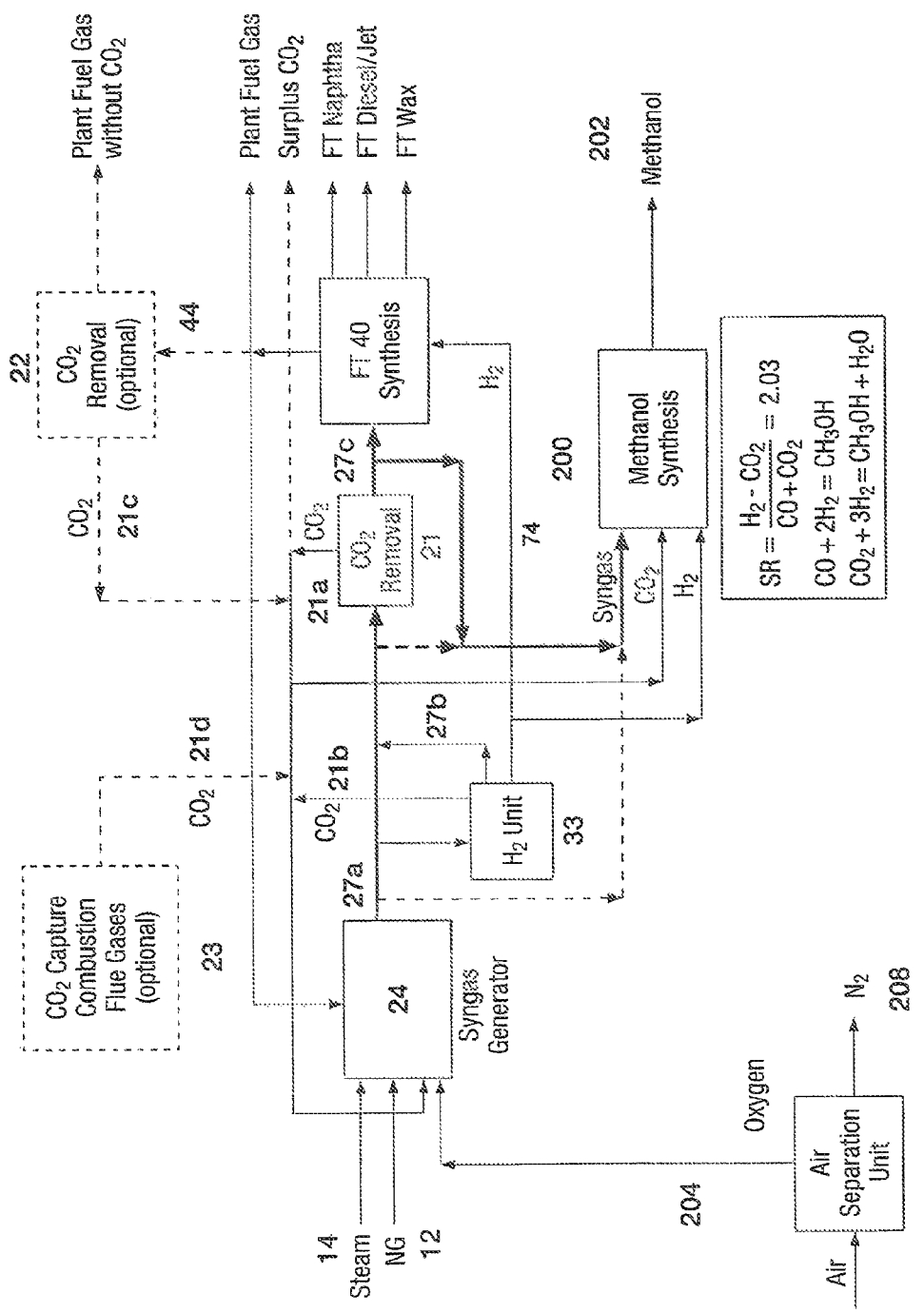
FIG. 7 is a process flow diagram illustrating integration of a methanol production unit with the hydrocarbon synthesis process in accordance with the present invention.

FIG. 7 describes one configuration of the present invention whereby a Methanol Synthesis Unit receives base syngas feed from the Syngas Generators as generally described in FIGS. 1 to 6, and is combined with the feed of excess $CO_2$ and $H_2$ to create the optimum methanol syngas feed stream, wherein optimum methanol synthesis stoichiometric ratio is defined as;

$$(H_2-CO_2)/(CO+CO_2)=2.03$$

With further processing the methanol can be used to produce numerous products such as DME gasoline/diesel, formaldehyde, MTBE, acetic acid, etc.

In further details, in the embodiment shown in FIG. 7, natural gas 12 and/or steam 14 and/or oxygen 204 are used as a feedstock to a syngas generator(s) 24 to generate a first hydrogen rich syngas stream 27a, where the ratio of hydrogen to carbon monoxide is in the range of about 2:1 to about 6:1. The hydrogen rich syngas generator 24 is typically composed of a steam methane reformer (SMR) or an auto thermal reformer (ATR) or parallel or series combinations thereof. Alternatively, the syngas generator 24 can be as a hybrid combination of an ATR/SMR referred to as a XTR.

A portion of the first hydrogen rich syngas stream 27a can be subjected to hydrogen separation unit 33 to generate a purified hydrogen by-product stream 74 and a second hydrogen rich syngas stream 27b. The second hydrogen rich syngas stream 27b has a hydrogen to carbon monoxide ratio less than that of the first hydrogen rich syngas stream 27a.

Any portion of the first hydrogen rich syngas stream 27a and the second hydrogen rich syngas stream 27b, or a combination thereof, can be subjected to carbon dioxide removal unit 21 to generate purified hydrogen rich syngas stream 27c and a carbon dioxide byproduct stream 21a.

In one embodiment a combination of the first hydrogen rich syngas stream 27a and the second hydrogen rich syngas stream 27b is fed to the carbon dioxide removal unit 21.

In one embodiment, after removal of carbon dioxide, the first hydrogen rich syngas stream 27a and the second hydrogen rich syngas stream 27b can be combined to obtain purified hydrogen rich syngas stream 27c and the carbon dioxide by-product stream 21a.

The first hydrogen rich syngas stream 27a and the second hydrogen rich syngas stream 27b are combined before or after $CO_2$ removal in unit 21 to create an optimum Fischer-Tropsch syngas stream where the preferred ratio of the hydrogen to carbon monoxide is 2:1. The purified hydrogen rich stream 27c is then fed to the Fischer-Tropsch upgrader unit 40 to formulate synthesized hydrocarbons.

Any portion of the first hydrogen rich syngas stream 27a, the second hydrogen rich syngas stream 27b, the purified hydrogen rich syngas stream 27c, or a combination thereof, can be reacted with carbon dioxide by-product stream 21a, or at least a portion of the purified hydrogen by-product stream 74, or a combination thereof to generate an optimum methanol feed stream to co-produce methanol 202 in methanol synthesis unit 200, in addition to the synthesized hydrocarbons as discussed above. The optimum feed stream for the methanol production involve the following reactions:

$$CO+2H_2=CH_3OH \text{ (primary reaction)}$$

$$CO_2+3H_2=CH_3OH \text{ (secondary reaction)}$$

wherein the optimum stoichiometric ratio is defined as $(H_2-CO_2/CO+CO_2)=2.03$ The purification of the first hydrogen rich stream 27a at hydrogen unit 33 can be achieved via pressure swing adsorption (PSA), membrane or liquid absorption technology or combination of above, or by treating the first hydrogen rich syngas stream to a water gas shift (WGS) reaction prior to pressure swing adsorption (PSA), membrane or liquid absorption with optional $CO_2$ removal unit for separate removal of an additional $CO_2$ by-product stream 21b. The $CO_2$ by-product stream 21b can optionally be removed from feed stream to PSA or after PSA from the tail gas. The $CO_2$ by-product stream 21b is removed directly as a by-product from the membrane and liquid absorption steps. The $CO_2$ by-product stream 21b can be used in the production of methanol 202, alone or in combination with the carbon dioxide stream 21a discussed above.

In a further embodiment, the unconverted FT Vapours 44 can be further treated in a $CO_2$ Removal unit 22 to create additional $CO_2$ by-product stream 21c. Additionally, a further optional embodiment is to provide separate or dedicated $CO_2$ Removal and Capture unit(s) 23 to recover additional $CO_2$ stream 21d from plant combustion flue gas sources from SMR furnaces, utility and power boilers and process furnaces using plant fuel gas made up of natural gas, plant off-gas streams, and or combinations of above. At least a portion of the additional $CO_2$ by-product streams 21c and 21d can be combined with the $CO_2$ by-product streams 21a and/or 21b to enhance the production of the methanol co-product.

Figure 8:
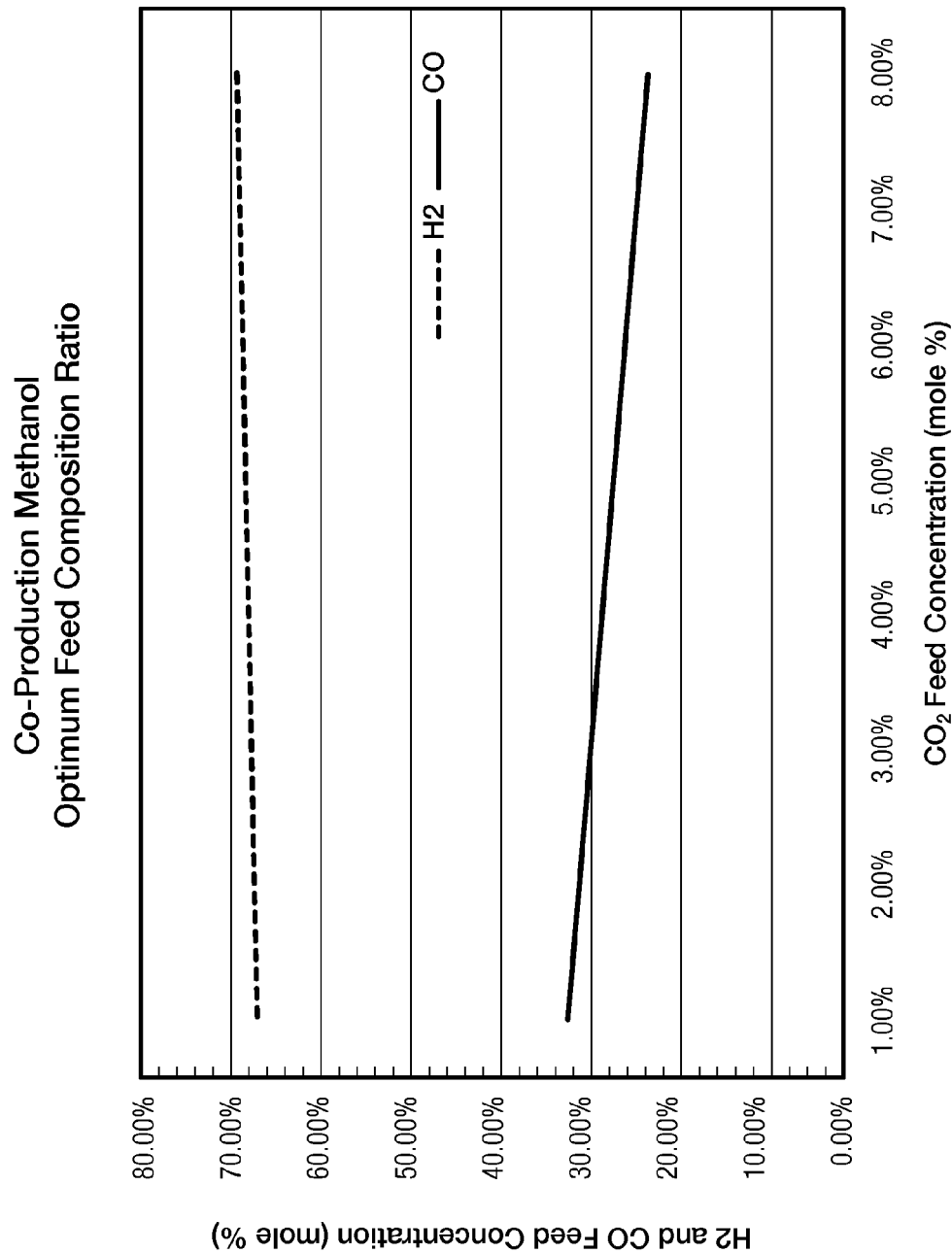
FIG. 8 is a chart illustrating the optimum feed composition for methanol production with the hydrocarbon synthesis process in accordance with the present invention.

FIG. 8 describes the optimum composition for syngas feeding the methanol synthesis unit based on the main active components CO, $H_2$ and $CO_2$, relative to the amount of $CO_2$ in the syngas.

Figure 9:
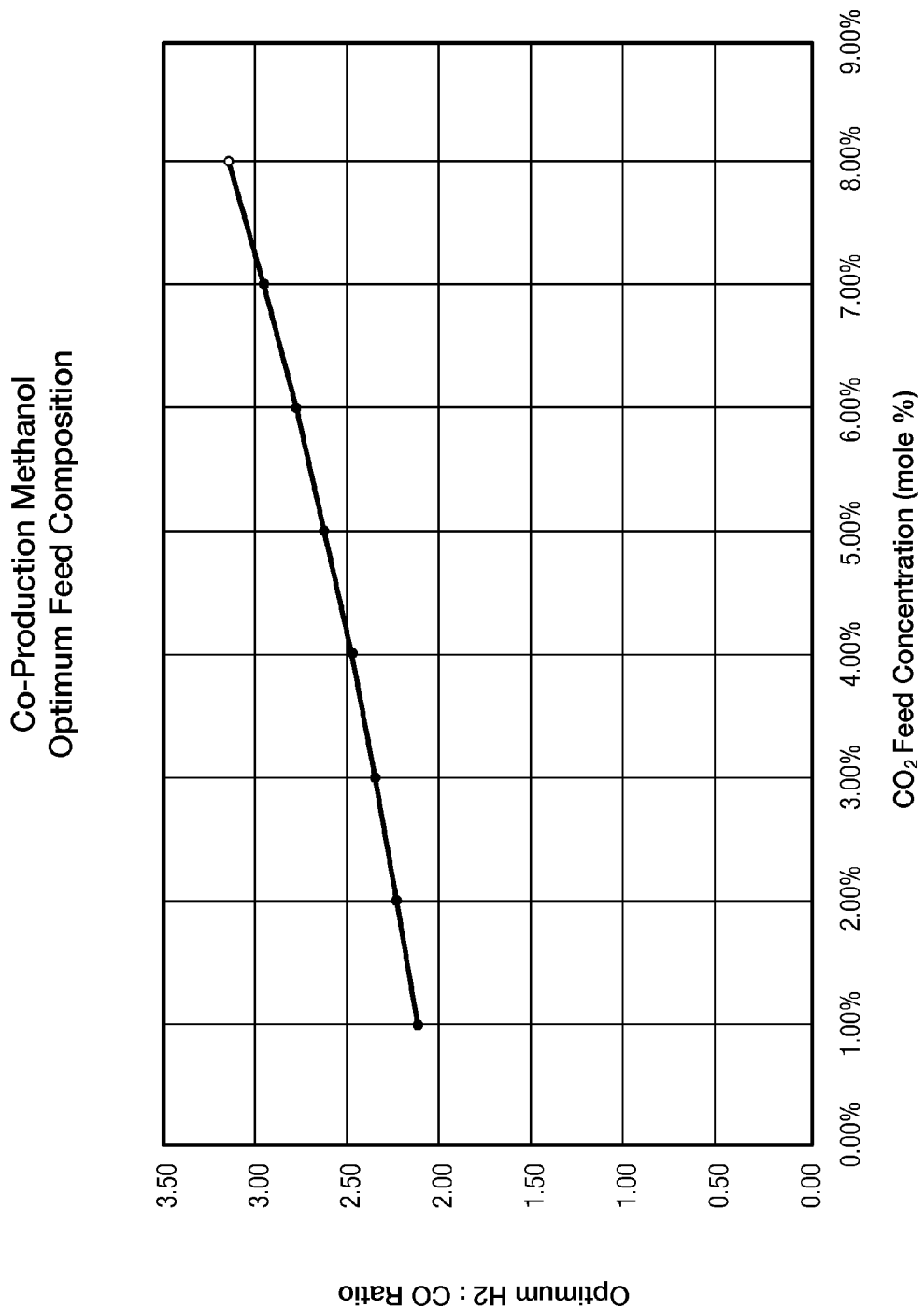
FIG. 9 is a chart illustrating the optimum stoichiometric $H_2$:CO feed ratio for methanol production with the hydrocarbon synthesis process in accordance with the present invention.

FIG. 9 further describes the optimum syngas $H_2$:CO ratios relative to the amount of $CO_2$ in the syngas. It is noted that for all methanol syngas feed streams, where the $CO_2$ content is greater than zero (typical and preferred), the $H_2$:CO ratio is always greater than 2.0, which is the optimum for Fischer-Tropsch synthesis.

The high purity oxygen 204, typically greater than 95% purity, more preferred greater than 98% purity, for use in the syngas generator 24, when the syngas generator comprises an ATR or POX, can be generated by subjecting air to an air separation unit (ASU) 206, along with the generation of a nitrogen by-product stream 208.

Figure 10:
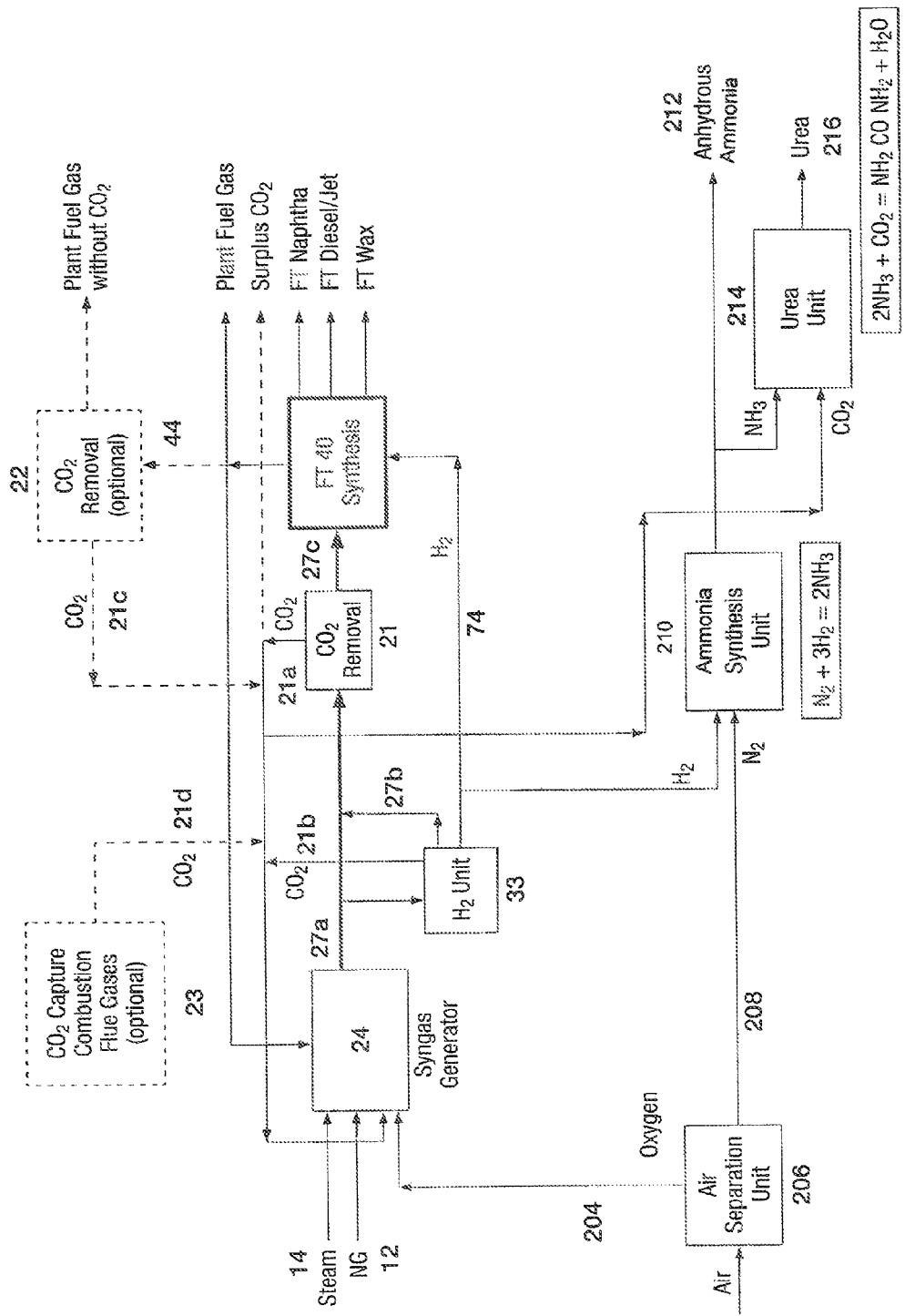
FIG. 10 is a process flow diagram illustrating integration of ammonia production with the hydrocarbon synthesis process in accordance with the present invention.

FIG. 10 describes one configuration of the present invention whereby an Ammonia Synthesis Unit receives excess hydrogen feed 74 from the Hydrogen Separation Unit 33, and combined with the feed of nitrogen by-product ($N_2$) 208, creates the optimum feed to produce anhydrous ammonia ($NH_3$) co-product.

$$N_2+3H_2=NH_3$$

With further processing and with the addition of by-product $CO_2$ from the hydrocarbon production, urea can be co-produced as follows;

$$2NH_3+CO_2=NH_2CONH_2+H_2O.$$

The process depicted in FIG. 10 is a variation of the process flow diagram depicted in FIG. 7, wherein at least a portion of the purified hydrogen by-product stream 74 is reacted with at least a portion of the nitrogen by-product stream 208 generated from the air separation unit 206, to produce ammonia 212 through an ammonia synthesis unit 210. The ammonia may then be optionally reacted with the carbon dioxide by-product streams 21a, 21b, 21c, 21d or any combination thereof to produce urea 216 through a urea synthesis unit 214.

Figure 11:
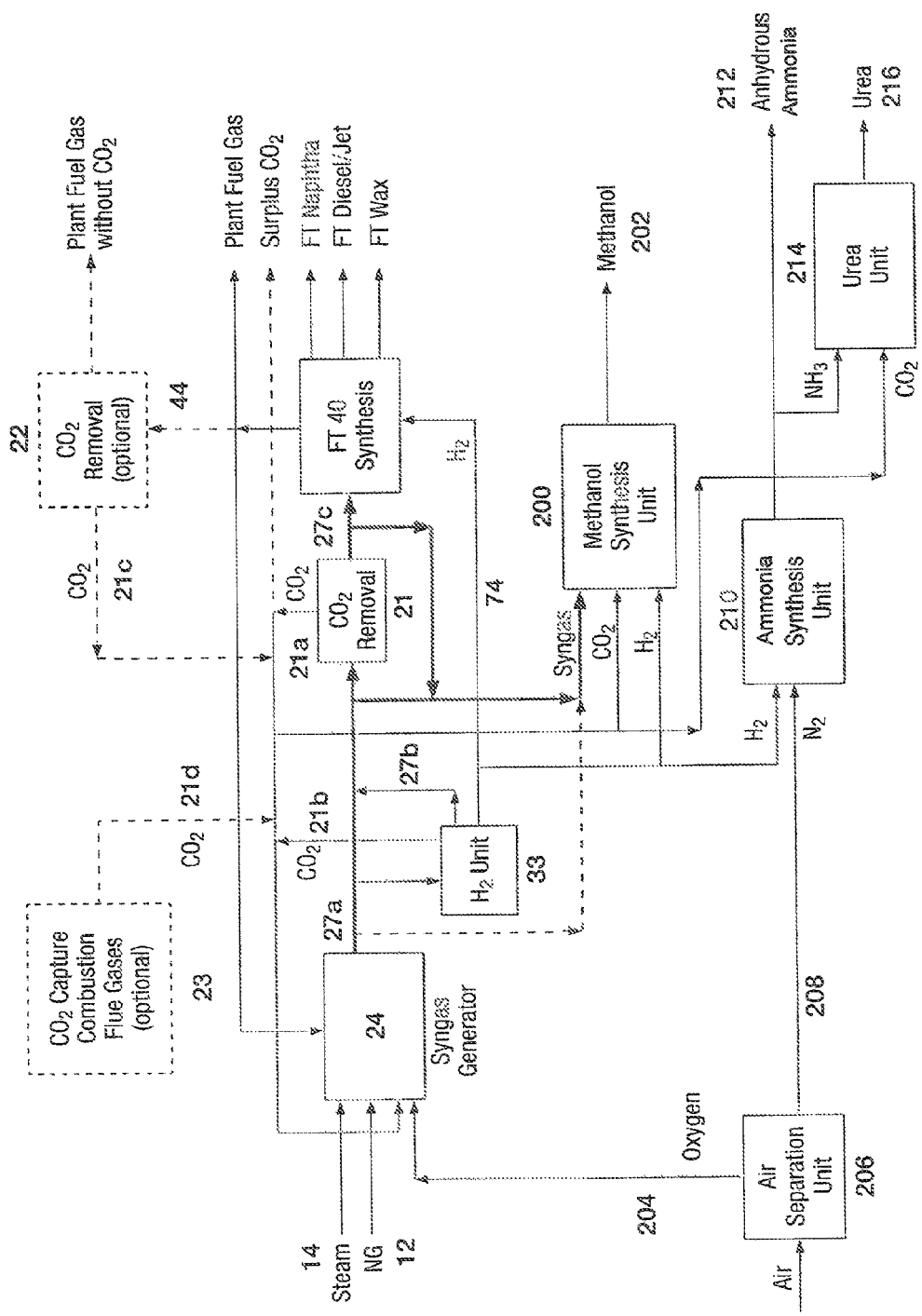
FIG. 11 is a process flow diagram illustrating integration of methanol and ammonia production with the hydrocarbon synthesis process in accordance with the present invention.

FIG. 11 describes another configuration of the present invention whereby Ammonia and Methanol Synthesis Units 210 and 200 as described in FIGS. 10 and 7, respectively, are integrated with the hydrocarbon production plant as described in FIGS. 1 through 6, and the combined processes produce synthetic diesel/jet, synthetic wax, ammonia and methanol, with optional further processing to obtain DME gasoline/diesel and urea fertilizer.

The following examples are based on a 104 MMSCFD dry pipeline natural gas (MW=17 and 2% $CO_2$) feed capacity 12, configured generally as described in U.S. application Ser. No. 13/228,042, filed Sep. 8, 2011. This GTL technology configuration is very efficient in retaining and converting carbon into about 10,000 BPD of synthetic hydrocarbon products from FT Synthesis unit 40 at an overall carbon conversion rate of greater than 65%. There is a by-product $CO_2$ stream 21a of about 1900 TPD available from the $CO_2$ Removal Unit 21 after the production of optimum rich hydrogen syngas stream 27c with $H_2$:CO ratio=2.0 for Fischer Tropsch synthesis (assuming minimal $CO_2$ in stream 27c). If The following Examples describe how valuable commercial co-products are produced according to one embodiment of the present invention.

Example 1

This example describes the design basis of a co-production Methanol Plant 200, whereby an additional portion of about 356 MMSCFD of syngas stream 27c is removed from the Fischer-Tropsch synthesis feed and directed as the base feed to unit 200. The natural gas 12 required by syngas generator 24 will be increased to about 50% to 204 MMSCFD and the by-product $CO_2$ stream 21a would increase to 3800 TPD. Combining a portion of about 656 TPD $CO_2$ from by-product stream 21a with about 40.6 MMSCFD $H_2$ from stream 74, the result would be the optimum feed for co-production of 5,000 TPD or 1,800,000 TPY of Methanol by-product. This is the current world scale commercial methanol plant.

a) Partial Stream 27c 356 MMSCFD or 39,035 moles/hr syngas with $H_2$:CO=2.0
b) Partial Stream 21a 656 TPD $CO_2$ or 1370 moles/hr $CO_2$
c) Partial Stream 74 40.6 MMSCFD $H_2$ or 4452 moles/hr $H_2$
d) The total syngas to Unit 200 44,856 moles/hr, or 67.94% $H_2$, 29.06% CO, 3.0% $CO_2$
e) Therefore, optimum syngas to Unit 200=(67.94−3.0)/29.06+3.0)=2.03
f) Total stream of 13,011 moles/hr CO+1,370 moles/hr $CO_2$+30,475 moles/hr $H_2$ results in 14,381 moles/hr $CH_3OH$ or about 460,000 lb/hr=5,000 TPD or 1,800,000 TPY methanol

Example 2

This example describes a design basis of a co-production Ammonia Plant 210, whereby the Air Separation Unit produces 3,900 TPD of high purity oxygen 206 for the ATR use. The subsequent by-product of nitrogen results in 15,300 TPD $N_2$ as stream 210. A portion of about 306 MMSCFD $H_2$ from stream 74 is combined with a portion of about 4,194 TPD $N_2$, the result would be the optimum feed for the co-production of 5,000 TPD or 1,800,000 TPY of Ammonia by-product. This is the current world scale commercial ammonia plant.

a) Partial Stream 208 consisting of 4,194 TPD $N_2$ or 11,333 moles/hr
b) Partial Stream 74 consisting of 306 MMSCFD $H_2$ or 33,553 moles/hr $H_2$
c) The total feed stream to Unit 210 of 44,886 moles/hr, or 25.2% $N_2$ and 74.8% $H_2$
d) 11,333 moles/hr $N_2$+33,553 moles/hr $H_2$ results in 22,666 moles/hr $NH_3$ or about 453,320 lb/hr=5,000 TPD or 1,800,000 TPY ammonia

Example 3

This example describes a design basis for a co-production Urea Plant 214, whereby a portion of the ammonia production 212 and additional by-product $CO_2$ from the GTL plant (21a, b, c or d) is combined to produce urea fertilizer.

a) Partial Stream 212 consisting of 4,202 TPD $NH_3$ or 19,048 moles/hr
b) A further portion of Stream 21a consisting of 3,144 TPD $CO_2$ and Partial Stream 21 b, c or d consisting of 1,417 TPD $CO_2$ for total of 4,561 TPD $CO_2$ or 9,524 moles/hr $CO_2$
c) The total feed stream to Unit 214 of 28,572 moles/hr, or 66.7% $NH_3$ and 33.3% $CO_2$
d) 19,048 moles/hr $NH_3$+9,524 moles/hr $CO_2$ results in 9,524 moles/hr $NH_2CONH_2$ or about 628,584 lb/hr=6,800 TPD or 2,400,000 TPY urea The examples described above illustrate how the integration of the co-product units can recover a significant portion of the GTL plant GHG $CO_2$ emissions and co-produce 5,000 TPD Methanol and 5,000 TPD Ammonia or 6,800 TPD of Urea, and result in a "Near Zero GHG Emissions World Class GTL plant".

These embodiments of the present invention can be used with all existing and new grassroots hydrocarbon production plants of any scale to enhance performance and economics.

The net effect of the present invention is that the hydrocarbon synthesis complex becomes:

The lowest cost producer of synthesized hydrocarbon products and co-products such as ammonia and methanol.

100% of all the carbon in captured $CO_2$ by-product streams can be converted to valuable commercial co-products.

The GTL Complex is "Near-Zero GHG Emission Green production plant"-best in class.

Although embodiments of the invention have been described above, it is not limited thereto and it will be apparent to those skilled in the art that numerous modifications form part of the present invention insofar as they do not depart from the spirit, nature and scope of the claimed and described invention.

The invention claimed is:

1. A process for synthesizing hydrocarbons in a Gas-to-Liquid (GTL) environment, and for co-producing chemical products from by-products of the hydrocarbon synthesis process, comprising the steps of:
  (a) formulating a first hydrogen rich syngas stream with a syngas generator, wherein said first hydrogen rich syngas stream has a $H_2$ to CO ratio of more than 2:1;
  (b) subjecting a portion of said first hydrogen rich syngas stream to a hydrogen separator unit to provide a purified hydrogen by-product stream and a second hydrogen rich syngas stream, wherein said second hydrogen rich syngas stream has a $H_2$ to CO ratio less than the $H_2$ to CO ratio of said first hydrogen rich syngas stream;
  (c) subjecting at least a portion of said first hydrogen rich syngas stream, at least a portion of said second hydrogen rich syngas stream, or a combination thereof, to a carbon dioxide removal operation to obtain purified hydrogen rich syngas stream and one or more carbon dioxide by-product streams;
  (d) reacting at least a portion of said first hydrogen rich stream, at least a portion of said second hydrogen rich stream and/or at least a portion of said purified hydrogen rich syngas stream in a Fischer-Tropsch reactor to synthesize said hydrocarbons; and
  (e) converting said one or more carbon dioxide by-product streams into said chemical co-products.

2. The process according to claim 1, wherein said chemical co-products comprise methanol, ammonia, urea or any combination thereof.

3. The process according to claim 1, wherein said syngas generator comprises a steam methane reformer (SMR), an autothermal reformer (ATR), any series or parallel combination thereof, or a merged unit (XTR) having an autothermal reformer merged in a single unit with a steam methane reformer.

4. The process according to claim 1, comprising subjecting air to an air separation unit to generate a nitrogen stream and an oxygen stream, wherein said oxygen stream is for the syngas generator when said generator comprises an ATR.

5. The process according to claim 1, wherein said chemical co-product is methanol, which is obtained by reacting a portion of said first hydrogen rich syngas stream, a portion of said second hydrogen rich syngas stream, a portion of said purified hydrogen rich syngas stream, or a combination thereof, with at least a portion of said one or more $CO_2$ by-product streams, or at least a portion of said purified hydrogen by-product stream or a combination thereof.

6. The process according to claim 4, wherein said chemical co-product is urea, which is obtained by reacting said nitrogen stream with at least a portion of said purified hydrogen by-product stream to form ammonia and reacting said ammonia with said one or more $CO_2$ by-product streams.

7. The process according to claim 1, wherein said purified hydrogen by-product stream is obtained by purification of at least a portion of said first hydrogen rich syngas stream via pressure swing adsorption, membrane or liquid absorption, or by treating at least a portion of said first hydrogen rich syngas stream to a water gas shift (WGS) reaction prior to pressure swing adsorption, membrane or liquid absorption with optional removal of an additional $CO_2$ by-product stream from the said second hydrogen rich stream.

8. The process according to claim 7, wherein the additional $CO_2$ by-product stream is used for conversion into said chemical co-products.

9. The process according to claim 1, wherein said hydrocarbons include at least naphtha, and wherein at least a portion of said naphtha is re-circulated to said syngas generator.

10. The process according to claim 1, wherein said hydrocarbons include at least one of Fischer-Tropsch vapours, paraffinic Fischer-Tropsch naphtha, light Fischer-Tropsch liquid, heavy Fischer-Tropsch liquid, or Fischer-Tropsch wax.

11. The process according to claim 10, wherein said Fischer-Tropsch vapours are further treated to a $CO_2$ removal operation to form an additional $CO_2$ by-product stream for conversion into said commercially valuable co-products.

12. The process according to claim 1, further including the step of processing said hydrocarbons in a hydroprocessing unit.

13. The process according to claim 12, wherein said hydroprocessing unit includes at least one operation selected from the group consisting of hydrocracking, thermocracking, hydrotreating, isomerization, fractionation and combinations thereof.

14. The process according to claim 1, wherein $CO_2$ is further captured in a $CO_2$ removal operation from flue gas streams resulting from syngas generator or any other furnaces, boilers, power generation and any other combustion units used in the hydrocarbon synthesis process to form an additional $CO_2$ by-product stream for conversion into said chemical co-products.

15. The process according to claim 1, further comprising providing $CO_2$ from any other external source other than the hydrocarbon synthesis process to form an additional $CO_2$ by-product stream for conversion into said chemical co-products.

16. The process according to claim 1, wherein the hydrocarbon synthesis process is capable of near zero green house gas $CO_2$ emissions.

* * * * *